(12) United States Patent
Cummings (10) Patent No.: US 8,895,707 B2
(45) Date of Patent: Nov. 25, 2014

(54) ELUTION OF PROTEINS FROM HYDROXYAPATITE RESINS WITHOUT RESIN DETERIORATION

(75) Inventor: Larry J. Cummings, Pleasant Hill, CA (US)

(73) Assignee: Bio-Rad Laboratories, Inc., Hercules, CA (US)

( * ) Notice: Subject to any disclaimer, the term of this patent is extended or adjusted under 35 U.S.C. 154(b) by 459 days.

(21) Appl. No.: 13/205,354

(22) Filed: Aug. 8, 2011

(65) Prior Publication Data

US 2012/0202975 A1 Aug. 9, 2012

Related U.S. Application Data

(60) Provisional application No. 61/374,750, filed on Aug. 18, 2010, provisional application No. 61/380,919, filed on Oct. 18, 2010.

(51) Int. Cl.

| | |
|---|---|
| *A23J 1/00* | (2006.01) |
| *B01D 15/38* | (2006.01) |
| *B01D 15/36* | (2006.01) |
| *C07K 1/22* | (2006.01) |
| *C07K 1/20* | (2006.01) |
| *C07K 1/18* | (2006.01) |
| *B01D 15/42* | (2006.01) |

(52) U.S. Cl.
CPC .............. *C07K 1/18* (2013.01); *B01D 15/3804* (2013.01); *B01D 15/426* (2013.01); *B01D 15/361* (2013.01); *C07K 1/22* (2013.01); *C07K 1/20* (2013.01)
USPC ............................ 530/412; 530/415; 530/416

(58) Field of Classification Search
None
See application file for complete search history.

(56) References Cited

U.S. PATENT DOCUMENTS

| | | | |
|---|---|---|---|
| 3,737,516 | A | 6/1973 | Jenner |
| 4,053,561 | A | 10/1977 | Irani |
| 4,859,342 | A | 8/1989 | Shirasawa et al. |
| 5,332,503 | A | 7/1994 | Lee et al. |
| 5,744,587 | A | 4/1998 | Alaska et al. |
| 5,783,217 | A | 7/1998 | Lee et al. |
| 6,156,178 | A | 12/2000 | Mansfield et al. |
| 6,602,697 | B1 | 8/2003 | Cook, III |
| 7,476,722 | B2 | 1/2009 | Vedantham et al. |
| 8,058,407 | B2 | 11/2011 | Sun et al. |
| 8,067,182 | B2 | 11/2011 | Kelley et al. |
| 2003/0166869 | A1 | 9/2003 | Vedantham et al. |
| 2004/0265298 | A1 | 12/2004 | Lin |
| 2005/0107594 | A1 | 5/2005 | Sun et al. |
| 2005/0209100 | A1 | 9/2005 | Duval et al. |
| 2006/0246544 | A1 | 11/2006 | Kang et al. |
| 2009/0047723 | A1 | 2/2009 | Jensen et al. |
| 2009/0186396 | A1 | 7/2009 | Gagnon |
| 2009/0187005 | A1 | 7/2009 | Gagnon |
| 2009/0264651 | A1 | 10/2009 | Daly |
| 2009/0318674 | A1 | 12/2009 | Gagnon |
| 2010/0113751 | A1 | 5/2010 | Sun et al. |
| 2011/0178276 | A1 | 7/2011 | Cummings et al. |

FOREIGN PATENT DOCUMENTS

| | | |
|---|---|---|
| EP | 256836 A1 | 2/1988 |
| EP | 1081221 A1 | 3/2001 |
| EP | 2138505 B1 | 8/2014 |
| WO | WO 03/059935 A2 | 7/2003 |
| WO | WO 2006/099308 A2 | 9/2006 |
| WO | WO 2009/017491 A1 | 2/2009 |
| WO | WO 2010034442 A1 * | 4/2010 |
| WO | WO 2010/148143 A1 | 12/2010 |

OTHER PUBLICATIONS

Gorbunoff et al.; "The interaction of proteins with hydroxyapatite—I. Role of protein charge and structure"; 1984, Analytical Biochemistry, vol. 136, No. 2, pp. 425-432.
International Search Report from PCT/US2011/048082, dated Mar. 20, 2012.
International Search Report from PCT/US2011/021158, dated Mar. 17, 2011.
International Search Report and Written Opinion from PCT/US2012/023512, dated May 10, 2012.
U.S. Appl. No. 13/006,022, filed Jan. 13, 2011 (25 pages).
U.S. Appl. No. 13/363,670, filed Feb. 1, 2012 (14 pages).
U.S. Appl. No. 13/891,502, filed May 10, 2013 (30 pages).
Office Action from U.S. Appl. No. 13/006,022, dated Jun. 29, 2012.
Office Action from U.S. Appl. No. 13/006,022, dated Nov. 15, 2012.
Office Action from U.S. Appl. No. 13/363,670, dated Mar. 11, 2013.
Office Action from U.S. Appl. No. 13/363,670, dated Sep. 21, 2012.
International Search Report from PCT/US2013/40591, dated Oct. 8, 2013.
Office Action from U.S. Appl. No. 13/363,670, dated Jul. 2, 2013.
Office Action from U.S. Appl. No. 13/363,670, dated Nov. 15, 2013.
Britsch, "Purification of Flavanone 3 beta-Hydroxylase from *Petunia hybrida*: Antibody preparation and Characterization of a Chemogenetically Defined Mutant", *Archives of Biochemistry and Biophysics*, 276(2):348-354 (1990).
Extended European Search Report dated Jul. 18, 2014 for EP Application No. 12742721.9, 6 pages.
Extended European Search Report dated Jul. 21, 2014 for EP Application No. 11733384.9, 7 pages.

* cited by examiner

*Primary Examiner* — Daniel E Kolker
*Assistant Examiner* — James Rogers
(74) *Attorney, Agent, or Firm* — Kilpatrick Townsend & Stockton LLP (57) ABSTRACT

Proteins, including monoclonal antibodies, that have been retained on hydroxyapatite resins for purposes of protein separation, purification, or both, are eluted from the resins by a elution buffer that contains controlled amounts of calcium and phosphate ions. The buffer allows elution to be performed in repeated runs at an acidic pH without deterioration of the resin.

11 Claims, 9 Drawing Sheets

ELUTION OF PROTEINS FROM HYDROXYAPATITE RESINS WITHOUT RESIN DETERIORATION

CROSS-REFERENCE TO RELATED APPLICATIONS

This application claims the benefit of U.S. Provisional Patent Application No. 61/374,750, filed Aug. 18, 2010, and U.S. Provisional Patent Application No. 61/380,919, filed Sep. 8, 2010. The contents of both provisional applications are incorporated herein by reference.

BACKGROUND OF THE INVENTION

1. Field of the Invention

This invention relates to hydroxyapatite resins and their use in protein elutions.

2. Description of the Prior Art

Hydroxyapatite is known to be useful in the separation and purification of proteins using retention protocols that involve affinity, ion exchange or hydrophobic interactions. Hydroxyapatite is particularly useful in the purification of recombinant proteins from host cell proteins, aggregates, endotoxin, and DNA. Protein loading of a hydroxyapatite column is commonly conducted at pH 6.5 with phosphate buffer at 2 mM to 5 mM, conditions that promote the adsorption of protein to the hydroxyapatite surface. In some cases, adsorption is further promoted by the inclusion of minor amounts of NaCl or KCl. Prior to protein loading, the resin is commonly equilibrated with a buffer of the same strength as the loading buffer and at the same pH. The equilibration and loading buffers both saturate the hydroxyapatite surface with hydroxonium ions ($H_3O^+$). Unfortunately, these ions tend to desorb during protein elution due to the acidic conditions that are typically encountered during the elution, and this causes the resin to deteriorate over time.

SUMMARY OF THE INVENTION

It has now been discovered that the deterioration of hydroxyapatite, including ceramic hydroxyapatite, during protein elution can be mitigated by eluting adsorbed proteins from the resin without causing the resin to deteriorate. The useful life of a hydroxyapatite resin is thus extended, and a single resin can be used to separate and purify proteins from a succession of samples. The elution of adsorbed proteins is achieved by the use of an elution buffer that contains a combination of calcium ions and phosphate ions at acidic conditions of about pH 6.0 or below, including acidities at which hydroxyapatite otherwise dissolves. In certain implementations of the invention, sodium chloride is also included in the elution buffer for enhanced desorption of the protein. The choice of whether or not to include sodium chloride and its amount when included depend on the type of retentive interaction between the protein and the hydroxyapatite, such as for example an ion exchange interaction or a coordination chemistry interaction. It has also been discovered that monoclonal antibodies can be separated from high molecular weight aggregates, such as dimers and higher polymers of monoclonal antibodies, by cation exchange on hydroxyapatite by the use of an elution buffer that includes calcium phosphate and an alkali metal salt, at a pH within the range cited above, and particularly within the range of 5.3 to 5.8. Accordingly, disclosed herein are methods of eluting proteins and monoclonal antibodies from a ceramic hydroxyapatite solid phase, and further disclosed are buffers used to perform these elutions.

BRIEF DESCRIPTION OF THE DRAWINGS

FIGS. 2A-2C are profiles of an attempt at an ovalbumin elution using an elution buffer different from that of FIGS. 1A-1C.

FIGS. 3A-3C are profiles of an ovalbumin elution under conditions modified from those of FIGS. 2A-2C.

DETAILED DESCRIPTION

Calcium ion for inclusion in the elution buffers described herein can be supplied by any calcium salt that is soluble in the elution buffer, which is typically an aqueous solution, and that is inert to the other components of the elution buffer, the hydroxyapatite resin, and the proteins retained on the resin, and in many cases also the remaining components of the source solution from which the proteins are sought to be extracted. Calcium halide salts are convenient to use, and calcium chloride is particularly convenient. In certain embodiments of the concept herein, best results will be achieved with a calcium ion concentration in the elution buffer of from about 25 ppm to about 260 ppm. An alternate range is about 40 ppm to about 200 ppm, and a further alternate range is about 50 ppm to about 150 ppm.

Phosphate ion for inclusion in the elution buffers can likewise be supplied from any phosphate salt that is soluble in the elution buffer, which is again typically aqueous, and that is inert to the other components of the buffer, the resin, the proteins, and the remaining components of the source solution. Alkali metal or alkaline earth metal phosphates are convenient, with sodium phosphate as an example. In certain embodiments of the concept herein, best results will be achieved with a phosphate ion concentration in the elution buffer of from about 2 mM to about 40 mM, and for certain proteins the optimal range is from about 15 mM to about 35 mM.

As noted above, the optimal composition of the elution buffer may vary with the type of interaction by which the protein binds to the hydroxyapatite. In cases where the interaction is one of cation exchange, for example, the inclusion of sodium chloride, particularly at a high concentration such as one within the range of about 30 mM to about 2000 mM, will be beneficial. In cases where the interaction is one involving the formation of a calcium coordination complex such as by chelation chemistry, a buffer with a low sodium chloride concentration, or in certain cases a buffer that is devoid of sodium chloride, can be used most effectively. Within the guidelines in this and the preceding paragraphs, the optimal elution buffer composition for any particular protein or combination of proteins is readily determined by routine experimentation.

Elution buffers for use in purifying monoclonal antibodies from high-molecular-weight aggregates preferably include calcium ion at a concentration of from about 50 ppm to about 225 ppm, phosphate ion at a concentration of from about 5 mM to about 40 mM, and an alkali metal salt at a concentration of from about 0.3M to about 1.5M. Further preferred ranges are about 50 ppm to about 100 ppm for the calcium ion concentration, and about 0.4M to about 0.8M for the alkali metal salt. Preferred alkali metal salts are sodium and potassium salts, or alkali metal halides and nitrates. Sodium and potassium chloride are particularly preferred.

The elution buffer for all elutions and purifications herein will provide optimal results in most applications when its pH is within the range of from about 5.3 to about 5.8. The pH can be maintained within this range by the use of conventional buffers, examples of which are ethylenediamine tetraacetic acid (EDTA), succinate, citrate, aspartic acid, glutamic acid, maleate, cacodylate, 2-(N-morpholino)-ethanesulfonic acid (MES), N-(2-acetamido)-2-aminoethanesulfonic acid (ACES), piperazine-N,N'-2-ethanesulfonic acid (PIPES), 2-(N-morpholino)-2-hydroxy-propanesulfonic acid (MOPSO), N,N-bis-(hydroxyethyl)-2-aminoethanesulfonic acid (BES), 3-(N-morpholino)-propanesulfonic acid (MOPS), N-2-hydroxyethyl-piperazine-N-2-ethanesulfonic acid (HEPES), 3-(N-tris-(hydroxymethyl)methylamino)-2-hydroxypropanesulfonic acid (TAPSO), 3-(N,N-bis[2-hydroxyethyl]amino)-2-hydroxypropanesulfonic acid (DIPSO), N-(2-hydroxyethyl)piperazine-N'-(2-hydroxypropanesulfonic acid) (HEPPSO), 4-(2-hydroxyethyl)-1-piperazine propanesulfonic acid (EPPS), N-[tris(hydroxymethyl)-methyl]glycine (Tricine), N,N-bis(2-hydroxyethyl)glycine (Bicine), [(2-hydroxy-1,1-bis(hydroxymethyl)ethyl)amino]-1-propanesulfonic acid (TAPS), N-(1,1-dimethyl-2-hydroxyethyl)-3-amino-2-hydroxypropanesulfonic acid (AMPSO), tris(hydroxymethyl)aminomethane (Tris), and bis[2-hydroxyethyl]iminotris-[hydroxymethyl]methane (Bis-Tris). Other buffers known in the art may be used as well. The amount of any such buffer and the means of adjusting the pH to a desired value are well known or will be readily apparent to those skilled in the art.

Forms of hydroxyapatite that will benefit from the use of elution buffers described herein include hydrated hydroxyapatite gels such as Bio-Gel HT gel (suspended in sodium phosphate buffer), Bio-Gel HTP gel (a dried form of Bio-Gel HT), and DNA-grade Bio-Gel HTP (a dried form of Bio-Gel HT with a smaller particle size than Bio-Gel HTP), as well as ceramic hydroxyapatite (CHT), all available from Bio-Rad Laboratories, Inc. (Hercules, Calif., USA). Ceramic hydroxyapatite (CHT), which is utilized in the examples herein, is a chemically pure form of hydroxyapatite that has been sintered at high temperatures. Ceramic hydroxyapatite is spherical in shape, with particle diameters ranging from about 10 microns to about 100 microns, and is typically available at nominal diameters of 20 microns, 40 microns, and 80 microns. Ceramic hydroxyapatite is macroporous, and is available in two types: Type I, with a medium porosity and a relatively high binding capacity, and Type II, with a larger porosity and a lower binding capacity. Either porosity can be used, and the optimal porosity for any particular protein separation or purification will vary with the proteins or the composition of the source mixture. Any of the forms of hydroxyapatite can be used alone, rather than in admixture with another separation medium or support, and can be used in a non-functionalized form, whether naturally-occurring or hydrated.

When hydroxyapatite resins are used in successive protein separations with the elution buffers disclosed herein, the resins can be regenerated after each separation by conventional means to clean the resins of residual proteins and contaminants and to equilibrate the resins to the conditions to be used for protein retention and elution. Regeneration in many cases will thus include, for example, neutralization of the resin with an appropriate basic solution, followed by regeneration to a neutral pH, followed in turn by equilibration to a slightly acidic pH within the range best suited for protein retention and to a salt concentration when a salt is included. In general, hydroxyapatite resins can be used for ten or more, often 25 or more, and often 50 or more protein separations and elutions without loss of resin integrity and function.

EXAMPLE 1

Figure 1A:
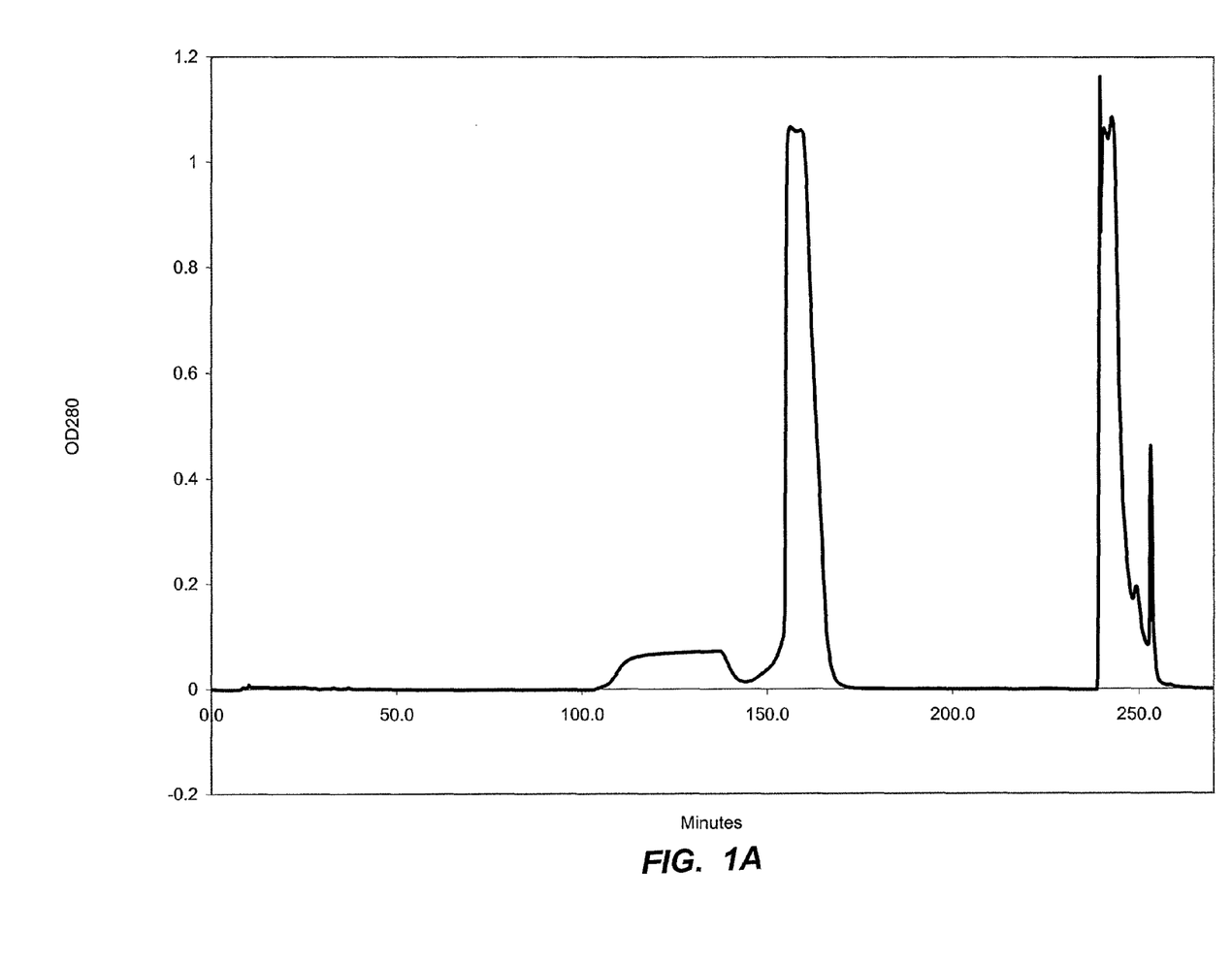
FIG. 1A is a profile of an ovalbumin elution using an elution buffer in accordance with the description herein, in the form of a plot of optical density vs. time.
Figure 1B:
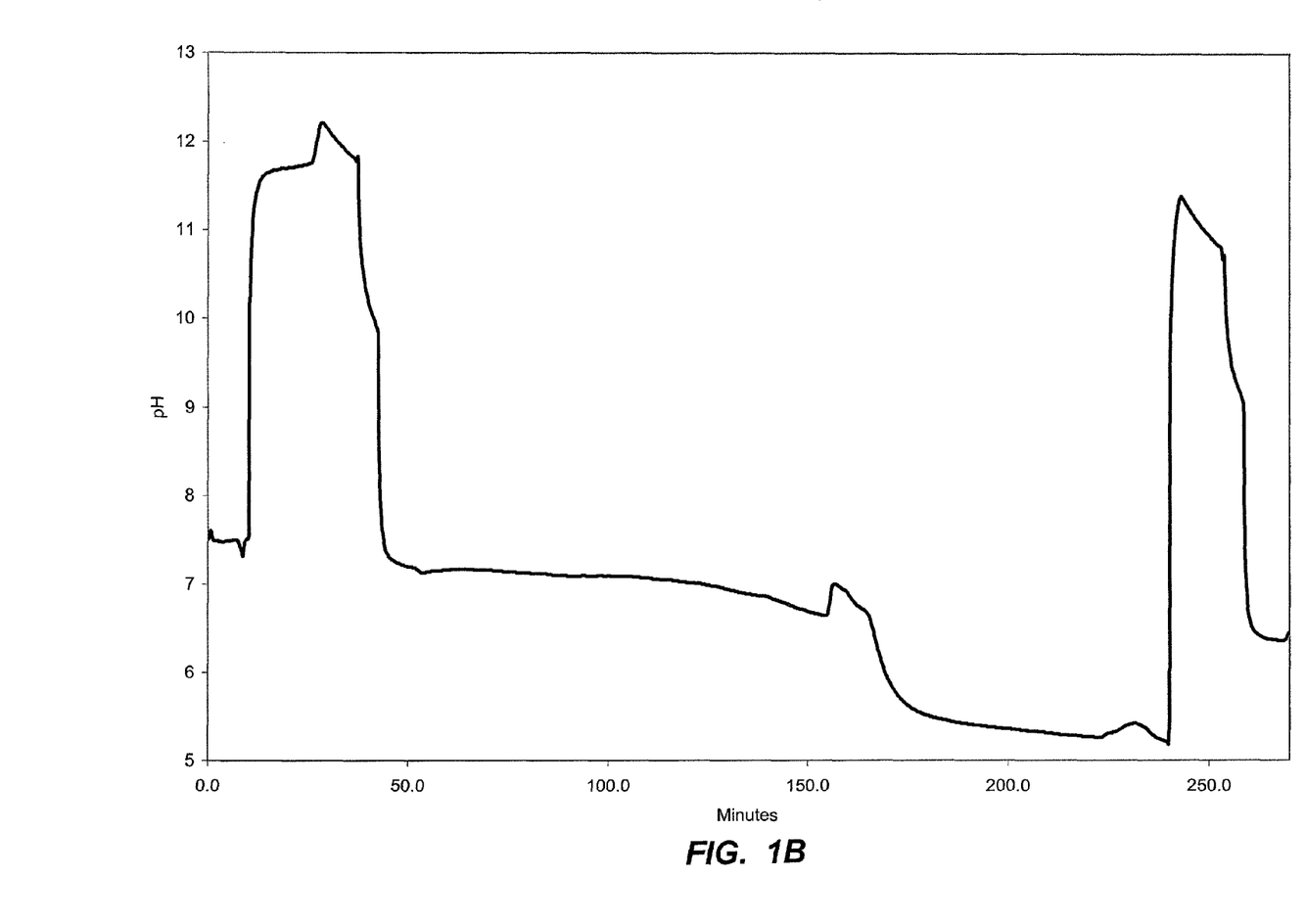
FIG. 1B is a plot of pH vs. time for the same elution.
Figure 1C:
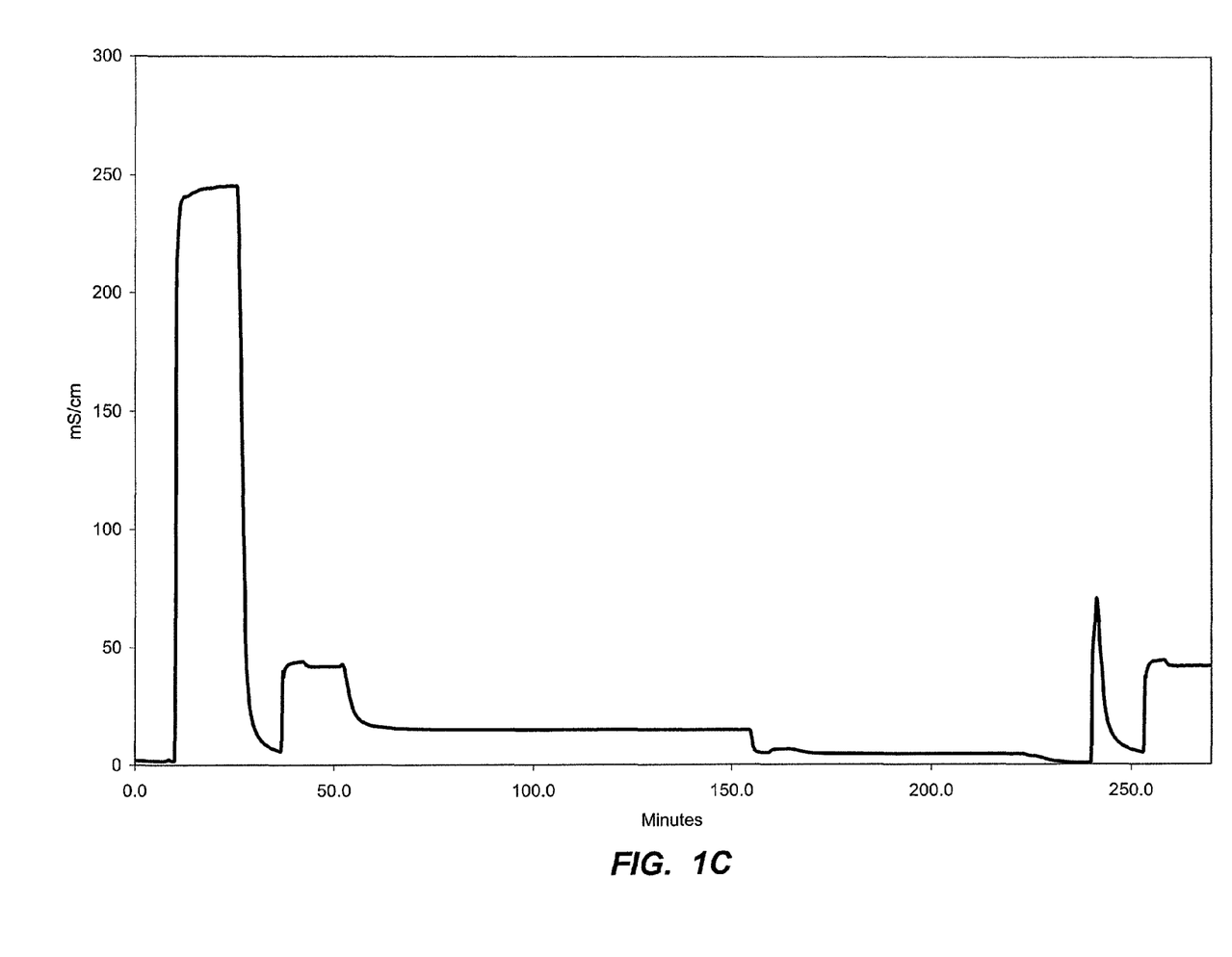
FIG. 1C is a plot of conductivity vs. time for the same elution.

Ovalbumin was bound to ceramic hydroxyapatite Type I in a column packed with approximately 12 grams of 40-micron particles of the hydroxyapatite, using an application buffer containing 5 mM phosphate ion and 100M NaCl at pH 6.5. The bound ovalbumin was then eluted by applying an elution buffer containing 3.0 mM calcium chloride, 30 mM phosphate, and 20 mM MES (2-(N-morpholino)-ethanesulfonic acid) at pH 5.6 (the elution buffer contained no NaCl). The elution profile is shown in FIGS. 1A, 1B, and 1C, FIG. 1A showing optical density vs. time, FIG. 1B showing pH vs. time, and FIG. 1C showing conductivity vs. time. Sanitization of the column was performed at twelve minutes, pH adjustment at 36 minutes, and protein loading at 108 minutes. Elution was begun at 154 minutes, followed by neutralization at 240 minutes and regeneration at 252 minutes. The low rise in optical density beginning at 108 minutes was an indication of a small amount of protein passing through the column unbound; the optical density peak beginning at 154 minutes represents the ovalbumin eluting from the column; and the optical density peaks beginning at the neutralization stage (240 minutes) represent the elution of contaminants in the ovalbumin.

This example demonstrates that ovalbumin can be eluted from hydroxyapatite at the conditions used.

EXAMPLE 2

Figure 2A:
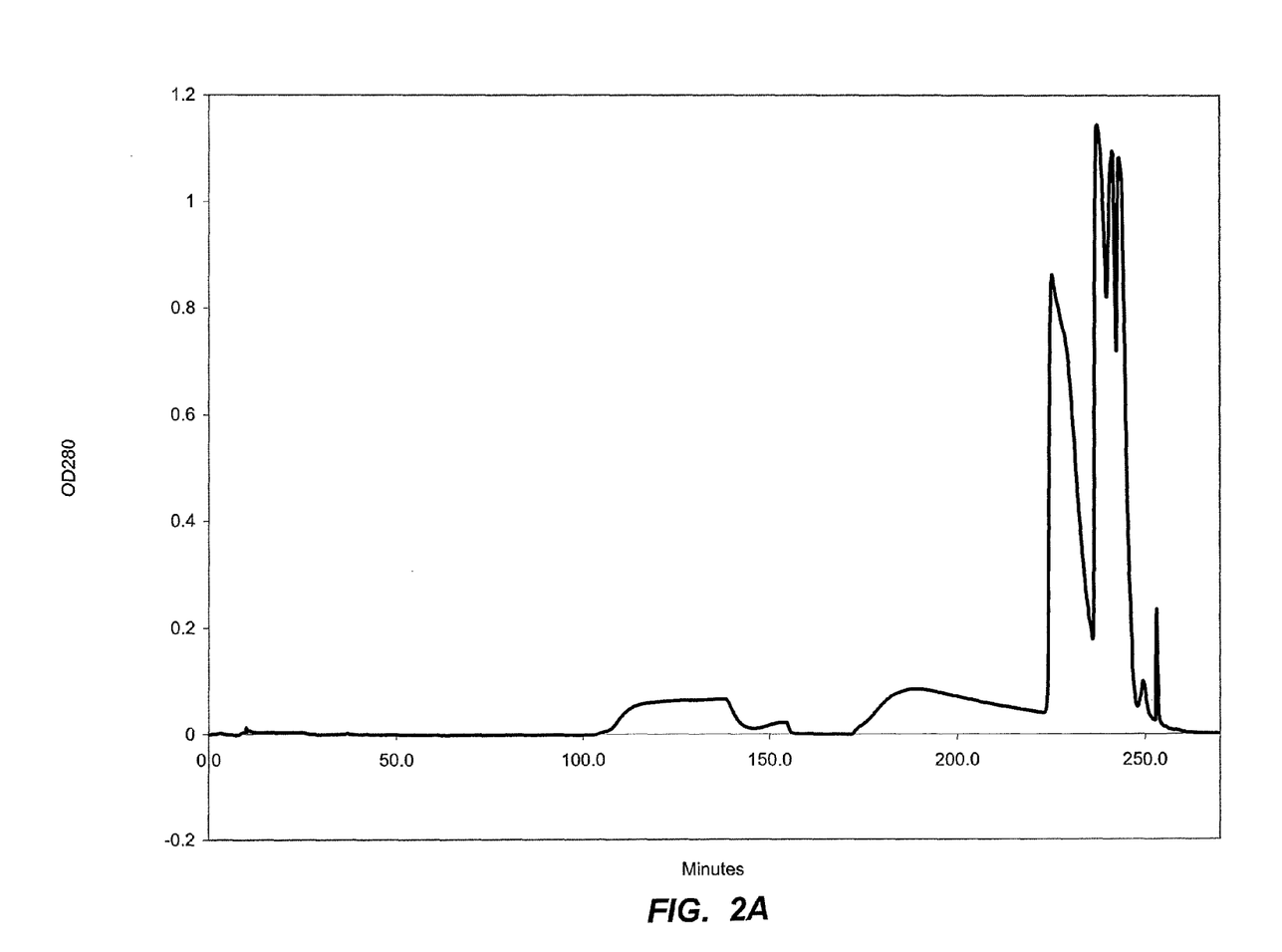
FIG. 2A is a plot of optical density vs. time.
Figure 2B:
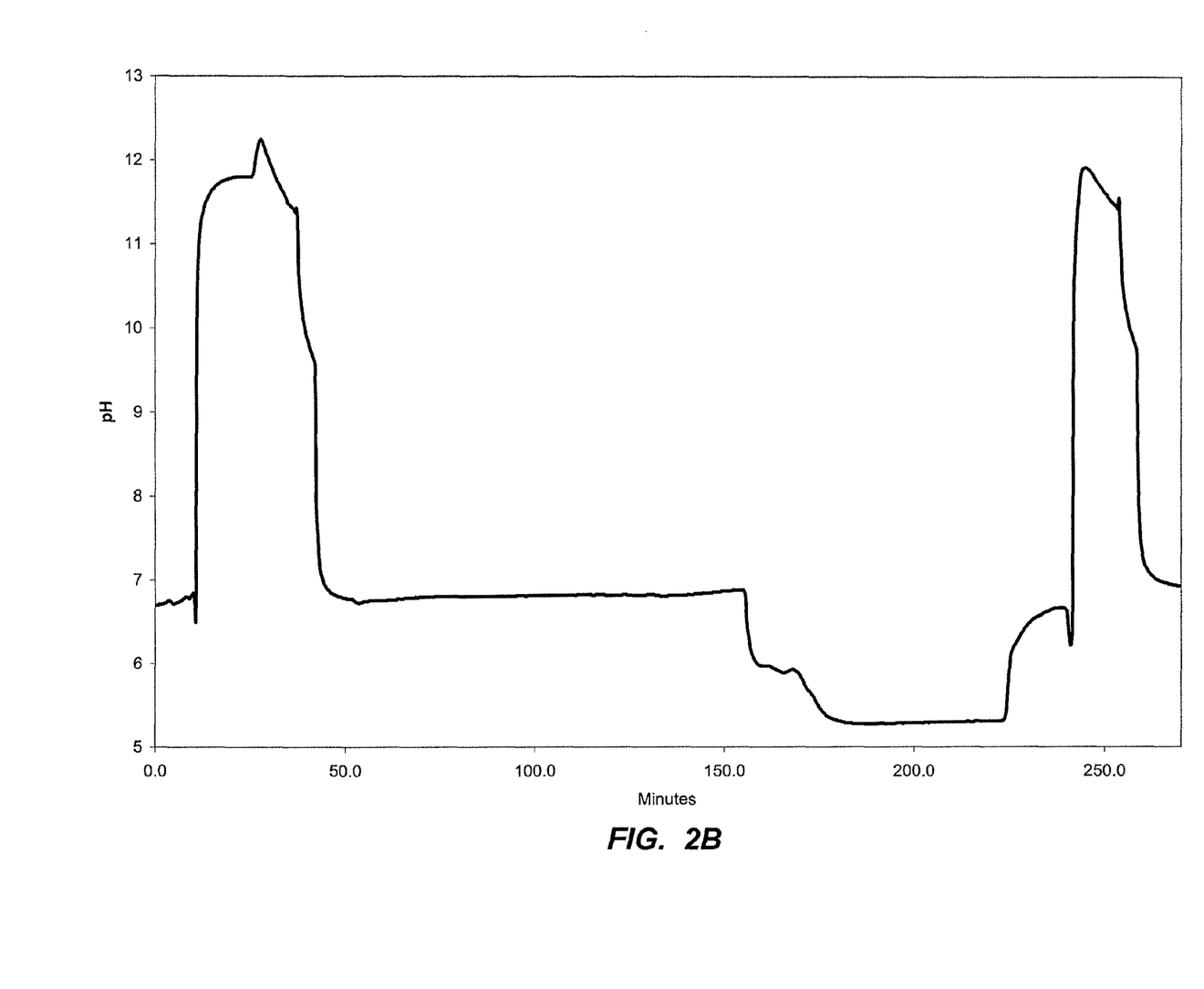
FIG. 2B is a plot of pH vs. time.
Figure 2C:
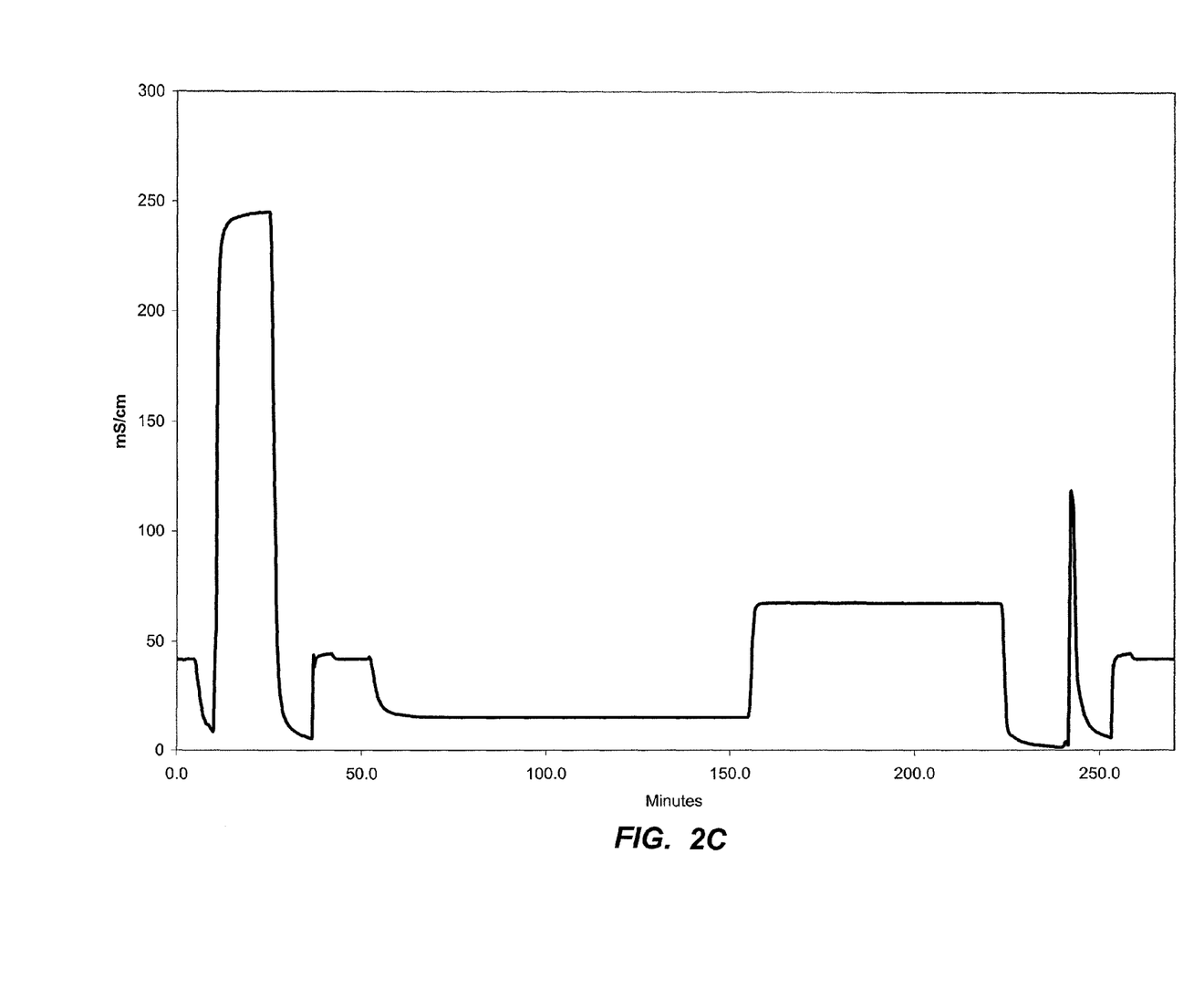
FIG. 2C is a plot of conductivity vs. time.

This example is a repeat of Example 1, except in a low-phosphate, high-salt elution buffer. The elution buffer 11 mM phosphate instead of 30 mM, and further contained 550 mM NaCl, all other components and operating conditions being the same. The elution profile is shown in FIGS. 2A, 2B, and 2C, representing optical density vs. time, pH vs. time, and conductivity vs. time, respectively. The low optical density rise beginning at 108 minutes was an indication of a small amount of protein passing through the column unbound, as in FIG. 1A; the optical density peaks beginning at neutralization (240 minutes) again represent contaminants in the ovalbumin.

The optical density trace shows that ovalbumin did not elute from the column with this elution buffer.

EXAMPLE 3

Figure 3A:
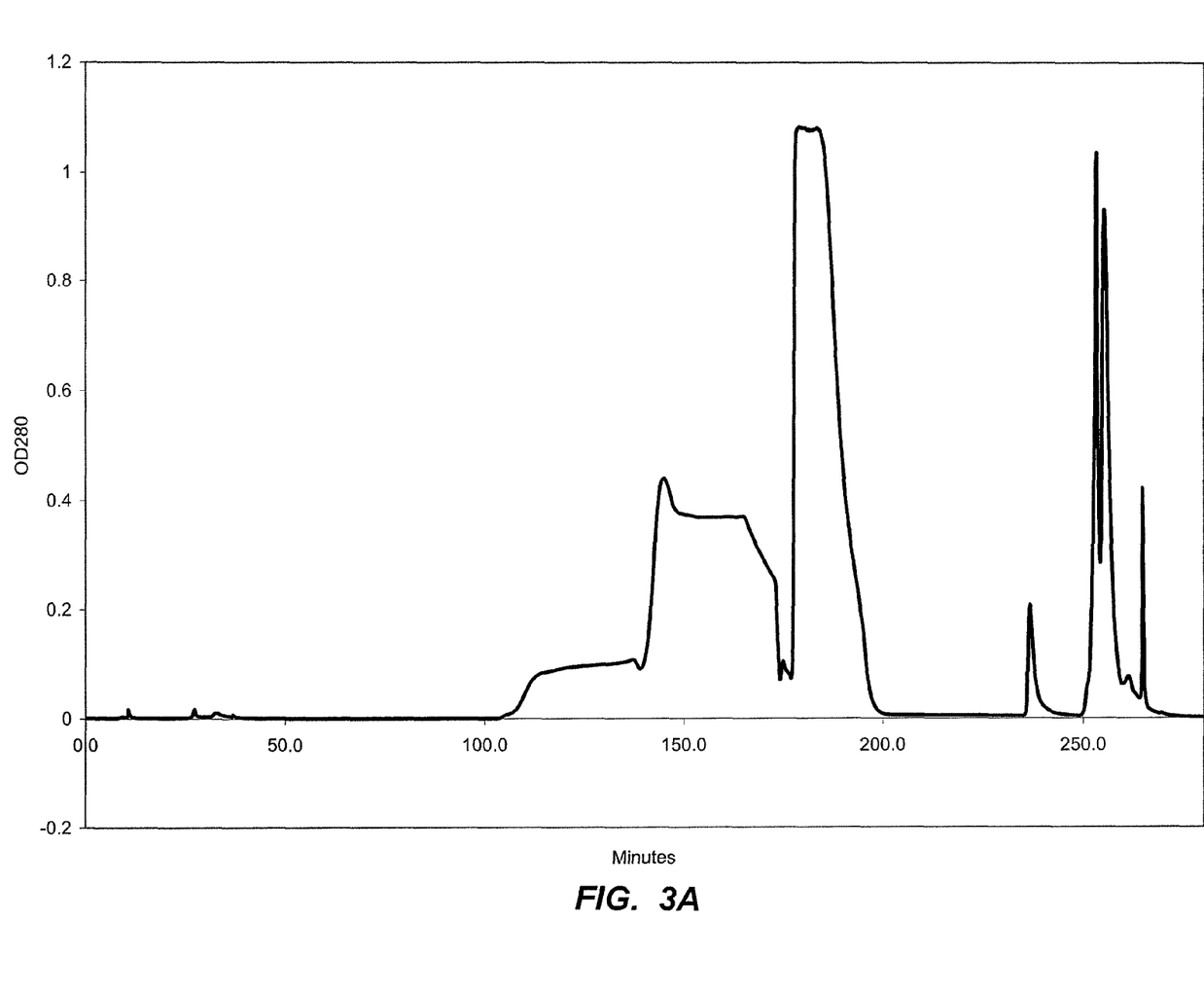
FIG. 3A is a plot of optical density vs. time.
Figure 3B:
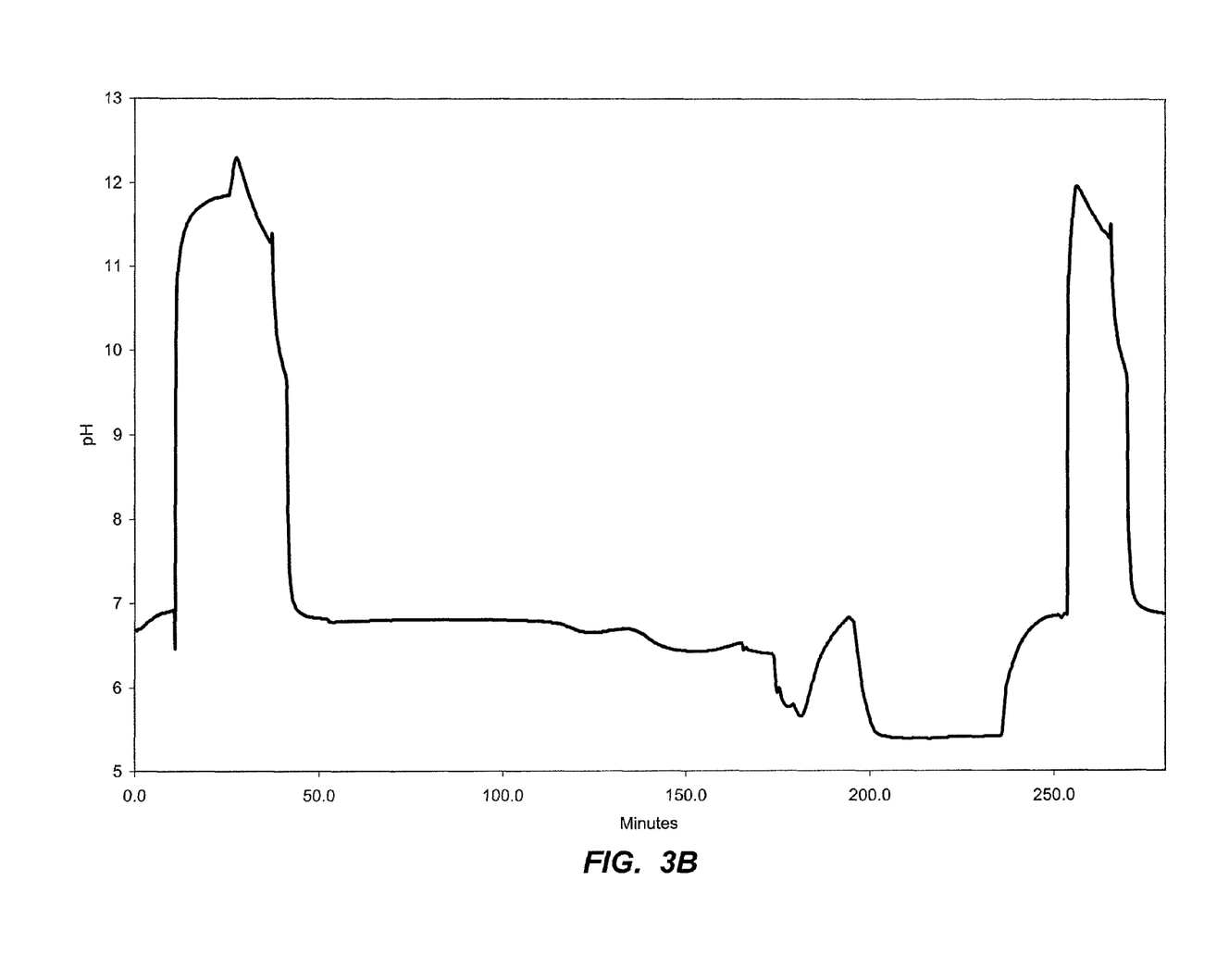
FIG. 3B is a plot of pH vs. time.
Figure 3C:
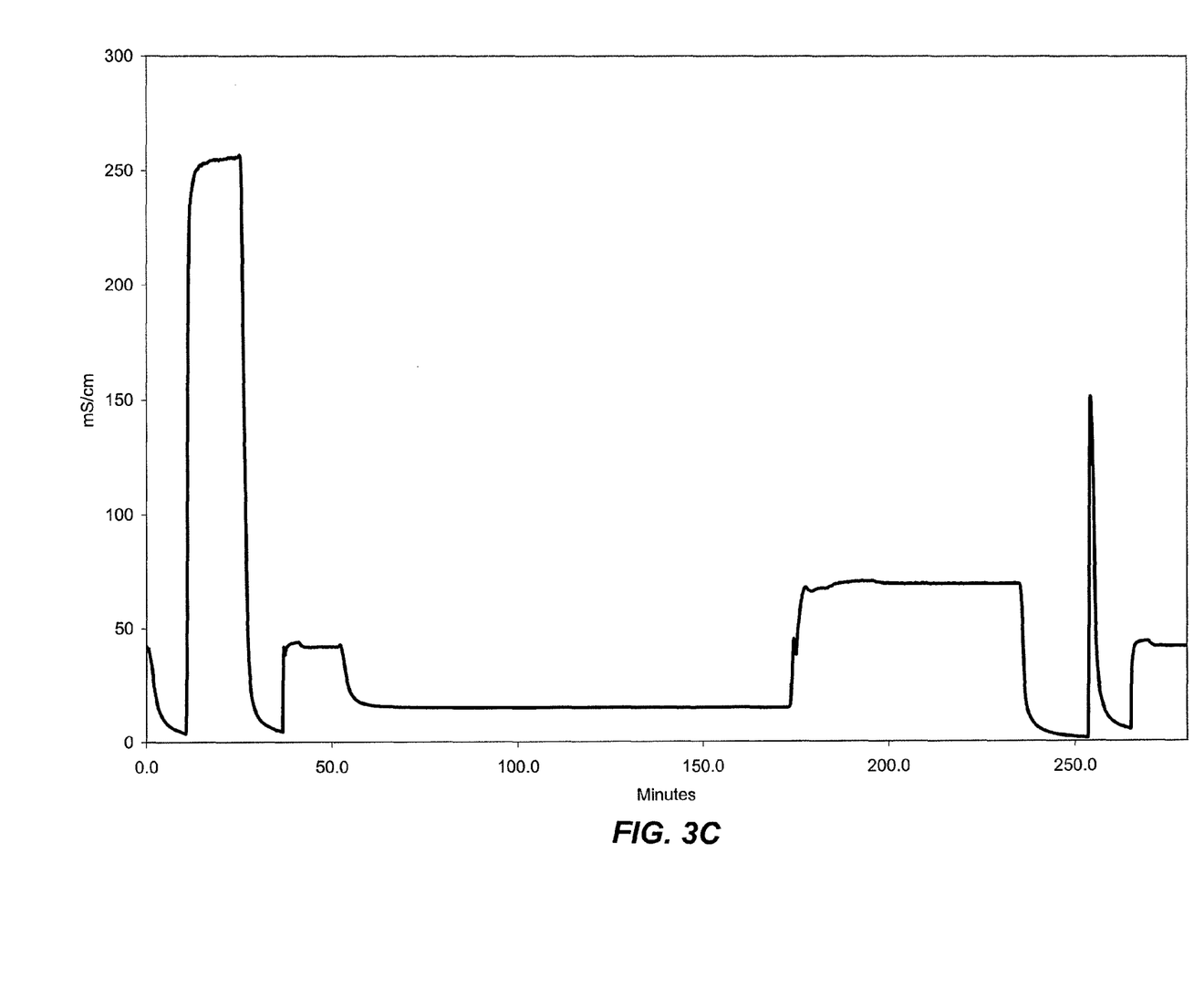
FIG. 3C is a plot of conductivity vs. time.

This example is a repeat of Example 2 with phosphate concentration in the elution buffer increased to 34 mM, all other materials and conditions being the same. The elution profile is shown in FIGS. 3A, 3B, and 3C, representing optical density vs. time, pH vs. time, and conductivity vs. time, respectively. Ovalbumin breakthrough due to overload of the column with ovalbumin is noticeable at 144 minutes, but the peak at 180 minutes indicates that desorption of ovalbumin from the column was restored with the higher-phosphate elution buffer.

EXAMPLE 4

This example illustrates the stability of ceramic hydroxyapatite over repeated exposures to an elution buffer containing 220 mM (220 ppm) calcium ion, 22.9 mM phosphate, 20 mM MES, and 0.55M NaCl at pH 5.6. As in the above examples, a column containing approximately 12 grams (specifically, 11.97 grams) of ceramic hydroxyapatite Type I of 40-micron particle diameter was used. The experiment was performed by passing the following sequence of materials through the column thirty-four (34) times (protein was not included):

TABLE I

Treatment Protocol for Ceramic Hydroxyapatite

| Stage | Treatment Material | Volume (mL) | Duration (min) |
|---|---|---|---|
| Sanitization | 1M NaOH | 38.0 | 17.1 |
| Cushion | Water | 19.0 | 8.6 |
| Regeneration | 0.4M Phosphate Buffer, pH 7.0 | 38.0 | 17.1 |
| Equilibration | 5 mM Phosphate Buffer, 0.1M NaCl, pH 6.5 | 114.0 | 51.4 |
| Application | 5 mM Phosphate Buffer, 0.1M NaCl, pH 6.5 | 76.0 | 34.3 |
| Wash | 5 mM Phosphate Buffer, 0.1M NaCl, pH 6.5 | 38.0 | 17.1 |
| Elution | 5.74 mM Ca, 22.9 mM Phosphate, 20 mM MES, 0.55M NaCl, pH 5.6 | 152.1 | 68.6 |
| Cushion | Water | 38.0 | 17.1 |
| Neutralization | 1M NaOH | 4.8 | 2.1 |
| Cushion | Water | 19.0 | 8.6 |
| Regeneration | 0.4M Phosphate Buffer, pH 7.0 | 57.0 | 25.7 |
| Cushion | Water | 19.0 | 8.6 |

Following the thirty-fourth cycle, the resin was removed from the column, cleaned, and weighed. The final weight was 13.36 g, representing a weight gain of 1.39 g. A small decrease in pore volume was observed, but since the particles were macroporous, this decrease would not affect the protein binding capability of the particles. The calcium ion content of the effluent ranged from 120-125 ppm, or about 95 ppm lower than the input value of 225 ppm.

While the above examples are directed to the retention and elution of ovalbumin, comparable results are achievable with other proteins. Examples of these proteins, in increasing order of isoelectric point, are α-lactalbumin, transferrin, bovine serum albumin, carbonic anhydrase, catalase, conalbumin, myoglobin, ribonuclease A, α-chymotrypsinogen A, lysozyme, and cytochrome c. Proteins with isoelectric points of 5.8 or above (such as conalbumin, myoglobin, ribonuclease A, α-chymotrypsinogen A, lysozyme, and cytochrome c) typically bind to, and are eluted from, hydroxyapatite by ion exchange, and elution of these proteins benefits from a high concentration of sodium chloride in the elution buffer. Proteins with isoelectric points below 5.8 (such as α-lactalbumin, transferrin, bovine serum albumin, carbonic anhydrase, and catalase) typically bind to hydroxyapatite by the formation of a calcium coordination complex, and elution of these proteins by decomplexation is best achieved when the phosphate concentration in the elution buffer is low.

EXAMPLE 5

This example illustrates the use of an elution buffer within the scope of this invention to purify monoclonal antibodies from high-molecular-weight aggregates on a hydroxyapatite column.

In a column measuring 22 cm in length with an internal diameter of 2.2 cm (column volume 83.63 mL and cross section area 3.803 cm$^2$) was placed 49.70 g ceramic hydroxyapatite Type I of 40-micron particle diameter. The resulting packed column had a flow rate of 175 cm/hour or 11.09 mL/min. A monoclonal antibody solution containing 5% high-molecular-weight aggregates (by weight) was used as the starting material. The sequence of materials passed through the column was as follows:

TABLE II

Monoclonal Antibody Purification Protocol

| Stage | Treatment Material | Volume (mL) | Duration (min) |
|---|---|---|---|
| Equilibration and Stabilization | 0.1M NaCl, 10 mM Na$_2$PO$_4$, pH 6.5 | 41.8 | 3.8 |
| | 500 mM Na$_2$PO$_4$, pH 7.5 | 167.3 | 15.1 |
| Equilibration and Stabilization | 0.1M NaCl, 10 mM Na$_2$PO$_4$, pH 6.5 | 585.4 | 52.8 |
| Application | MAb solution with 0.1M NaCl | 493.4 | 44.5 |
| Rinse | 0.1M NaCl, 10 mM Na$_2$PO$_4$, pH 6.5 or 20 mM MES, 10 mM Na$_2$PO$_4$, 1.5 mM (60 ppm) CaCl$_2$, pH 5.6 | 167.3 | 15.1 |
| Elution | 20 mM MES, 23 mM Na$_2$PO$_4$, 600 mM NaCl, 1.5 mM (60 ppm) CaCl$_2$, pH 5.6 | 1003.6 | 90.5 |
| Rinse | Water | 167.3 | 15.1 |
| Neutralization | 1N NaOH | 41.8 | 3.8 |
| Regeneration | 500 mM Na$_2$PO$_4$, pH 7.5 | 250.9 | 22.6 |
| Rinse | Water | 41.8 | 3.8 |
| Neutralization | 1N NaOH | 250.9 | 22.6 |

The content of high-molecular-weight aggregates in the MAb eluting from the column had been reduced to less than 0.6% by weight.

In the claims appended hereto, the term "a" or "an" is intended to mean "one or more." The term "comprise" and variations thereof such as "comprises" and "comprising," when preceding the recitation of a step or an element, are intended to mean that the addition of further steps or elements is optional and not excluded. All patents, patent applications, and other published reference materials cited in this specification are hereby incorporated herein by reference in their entirety. Any discrepancy between any reference material cited herein or any prior art in general and an explicit teaching of this specification is intended to be resolved in favor of the teaching in this specification. This includes any discrepancy between an art-understood definition of a word or phrase and a definition explicitly provided in this specification of the same word or phrase.

What is claimed is:

1. A method for eluting proteins from a solid phase comprising hydroxyapatite to which said proteins are bound, said method comprising passing through said solid phase an eluent comprising calcium ion at a concentration of from about 25 ppm to about 260 ppm and phosphate ion at a concentration of from about 2 mM to about 40 mM at a pH of from about 5.3 to about 5.8.

2. The method of claim 1 wherein said eluent further comprises sodium chloride at a concentration of from about 30 mM to about 2000 mM.

3. The method of claim 1 wherein said eluent is substantially devoid of sodium chloride.

4. The method of claim 1 wherein said calcium ion concentration is from about 40 ppm to about 200 ppm.

5. The method of claim 1 wherein said calcium ion concentration is from about 50 ppm to about 150 ppm.

6. The method of claim 1 wherein said phosphate ion concentration is from about 15 mM to about 35 mM.

7. The method of claim 1 wherein said hydroxyapatite is ceramic hydroxyapatite.

8. A method for extracting monoclonal antibodies from high-molecular-weight aggregates in a solution comprising said antibodies and aggregates, said method comprising:
   (i) applying said solution to a solid phase comprising hydroxyapatite, and
   (ii) passing through said solid phase an eluent comprising calcium ion at a concentration of from about 50 ppm to about 225 ppm, phosphate ion at a concentration of from about 5 mM to about 40 mM, and an alkali metal salt at a concentration of from about 0.3M to about 1.5N, at a pH of from about 5.3 to about 5.8 to obtain an eluate containing said monoclonal antibodies.

9. The method of claim 8 wherein said alkali metal salt is a member selected from the group consisting of a sodium halide, a potassium halide, a sodium nitrate, and a potassium nitrate.

10. The method of claim 8 wherein said alkali metal salt is a member selected from the group consisting of a sodium chloride and potassium chloride.

11. The method of claim 8 wherein said alkali metal salt is sodium chloride.

\* \* \* \* \*